United States Patent [19]
Steen et al.

[11] Patent Number: 5,511,451
[45] Date of Patent: Apr. 30, 1996

[54] WRENCH

[75] Inventors: Mark E. Steen, Chino Hills, Calif.;
Robert P. Gill, Rapid City, S. Dak.

[73] Assignee: Chiron Vision Corporation, Irvine, Calif.

[21] Appl. No.: 344,983

[22] Filed: Oct. 28, 1994

[51] Int. Cl.$^6$ ...................................................... B25B 13/06
[52] U.S. Cl. ............................................. 81/55; 81/124.4
[58] Field of Search ..................................... 81/124.2, 125, 81/121.1, 124.4, 124.5, 55, 13

[56] References Cited

U.S. PATENT DOCUMENTS

| | | | |
|---|---|---|---|
| 1,318,088 | 10/1919 | Klein | 81/55 |
| 1,507,362 | 9/1924 | Bartosik | 81/55 |
| 1,905,851 | 4/1930 | Green . | |
| 2,181,678 | 11/1939 | Wright | 81/55 |
| 2,249,906 | 9/1941 | Longoria . | |
| 2,598,060 | 1/1950 | Kadesky . | |
| 2,834,241 | 5/1958 | Chowning | 81/125 |
| 3,990,453 | 11/1976 | Douvas et al. . | |
| 4,329,892 | 5/1982 | Daigle | 81/55 |
| 4,526,067 | 7/1985 | Gaquére | 81/55 |
| 4,834,748 | 5/1989 | McDonald . | |
| 4,837,857 | 6/1989 | Scheller et al. . | |
| 4,908,015 | 3/1990 | Anis . | |
| 4,979,355 | 12/1990 | Ulevich | 81/125 X |
| 5,133,726 | 7/1992 | Ruiz et al. . | |
| 5,222,959 | 6/1993 | Anis . | |

OTHER PUBLICATIONS

PhacoTmesis™, A Chiron Vision White Paper, Update: AAO, 1993, pp. 1–9, ©1993.

*Primary Examiner*—D. S. Meislin
*Attorney, Agent, or Firm*—Banner & Allegretti, Ltd.

[57] ABSTRACT

A wrench for installing and removing a tip onto and from a tool comprises a rotary part and a locking hub. The tool includes a housing and a rotatable shaft which has a threaded bore. The tip includes a working portion and a threaded shank which is to be secured in the threaded bore of the shaft. The hub includes a projection which has a non-circular opening which engages a complementary surface on the shaft and a non-circular exterior surface which engages a complementary surface on the interior of the housing to prevent rotation of the shaft relative to the housing. The rotary part includes a passage which includes a non-circular portion which engages the tip to screw the tip into the shaft.

14 Claims, 4 Drawing Sheets

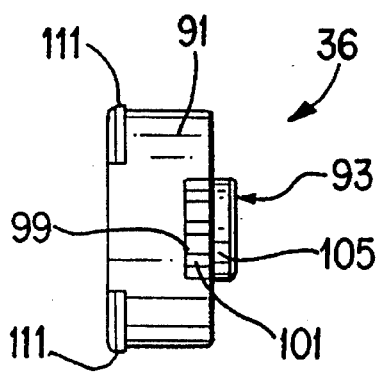
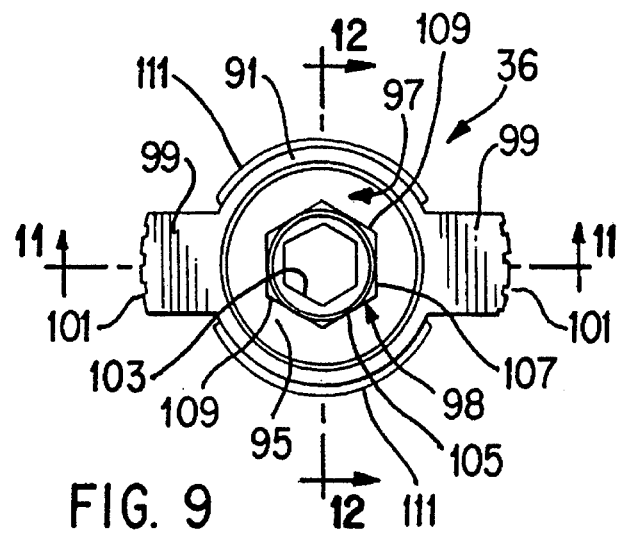
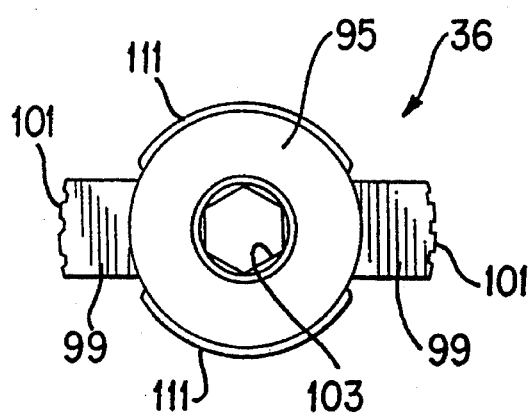
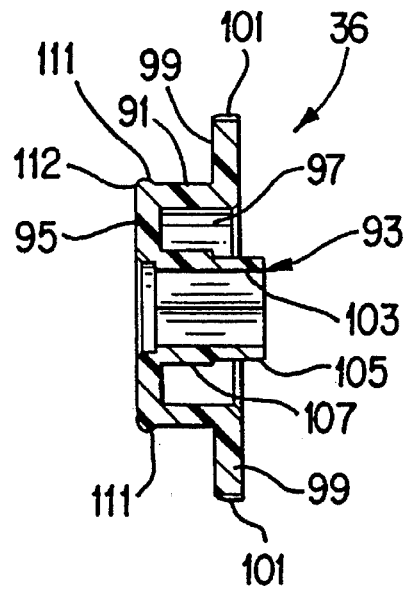
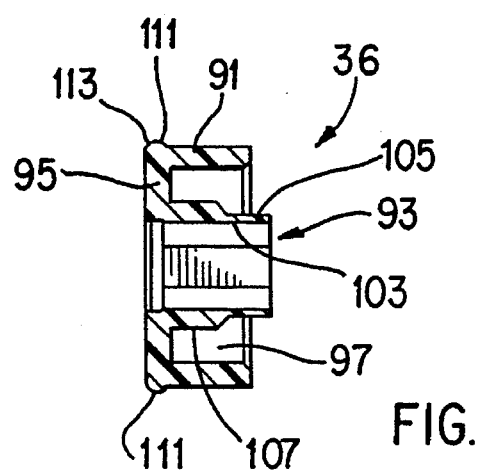

WRENCH

FIELD OF THE INVENTION

The present invention pertains to a wrench for the installation and removal of a tip onto and from a tool, and in particular, with respect to a tool for use in cataract surgery.

BACKGROUND OF THE INVENTION

The natural crystalline lens of the eye plays a primary role in focusing light onto the retina for proper vision. However, the lens can become damaged due to injury or become cloudy because of aging or disease and form a cataract. To restore vision to the eye, the natural lens must be surgically removed and an artificial lens implanted as a replacement.

Many surgical procedures have been developed for removing the natural lens. The use of small incision techniques tends to cause less trauma and fewer operative and post-operative complications. According to these procedures, a slender tool is inserted through a small incision made in the eye and into the natural lens. The distal tip of the tool functions to fragment the lens and then aspirate the lens material out of the eye through an internal duct. In one process, disclosed in U.S. Pat. No. 5,222,959, the tip is rotated to cut the lens into small pieces without damaging the capsular bag. In another process, known as phacoemulsification, the tip is subjected to ultrasonic vibrations to emulsify the lens. Alternatively, the tip may be an ultrasonically assisted rotary tip which cuts the lens by longitudinal and rotational motion.

Surgical devices for performing such operations are typically hand-manipulatable and comprise a housing, a central shaft, and a cutting or polishing tip. A plurality of tips can be interchangeably mounted onto the distal end of the shaft. The tips each include a working end for performing the cutting or polishing and a mounting end having a threaded shank. The shank is screwed into a threaded bore formed in the end of the shaft.

As can be appreciated, the tip must be securely attached to the shaft during the operation. To effect a tight connection, flats are provided on both the tip and the shaft to facilitate the engagement of each with a wrench. In one construction, a pair of opposite flats are formed on the tip adjacent the threaded shank, and a hexagonal nut segment is formed on the proximal end of the shaft which extends rearwardly beyond the housing. Accordingly, a pair of wrenches are used to tighten or loosen the tip onto the shaft. This is a cumbersome procedure which requires the user to manipulate a wrench in each hand as well as support and stabilize the tool.

SUMMARY OF THE INVENTION

The present invention pertains to a wrench for installing and removing a working tip onto and from a tool. The inventive wrench is especially designed to tighten or loosen a tip with respect to a device for performing cataract surgery. The wrench is easily operable with only one hand and obviates the need for a second wrench.

A wrench in accordance with the present invention is usable with a tool which comprises a housing, a rotatable shaft, and a removable tip threadedly attached to the shaft. The wrench includes a rotary part and a locking hub movable relative to each other. The rotary part is formed with an internal passage having at least a non-circular portion adapted to engage a complementary surface defined on the tip. The hub includes a projection which is adapted to be received within a gap defined between the shaft and the housing of the tool. The projection includes at least a non-circular portion on each of its inner and outer walls to engage complementary surfaces on the tool and thereby lock the shaft relative to the housing. In this way, the shaft is prevented from rotating as the tip is tightened or loosened.

These and other objects, advantages and features of the present invention will be more fully understood and appreciated by reference to the written specification and appended drawings.

BRIEF DESCRIPTION OF THE DRAWINGS

FIG. 8 is side view of the hub of the wrench.

FIG. 9 is a front view of the hub.

FIG. 10 is a rear view of the hub.

FIG. 11 is a cross-sectional view taken along line 11—11 in FIG. 9.

FIG. 12 is a cross-sectional view taken along line 12—12 in FIG. 9.

DETAILED DESCRIPTION OF THE PREFERRED EMBODIMENT

Figure 13:
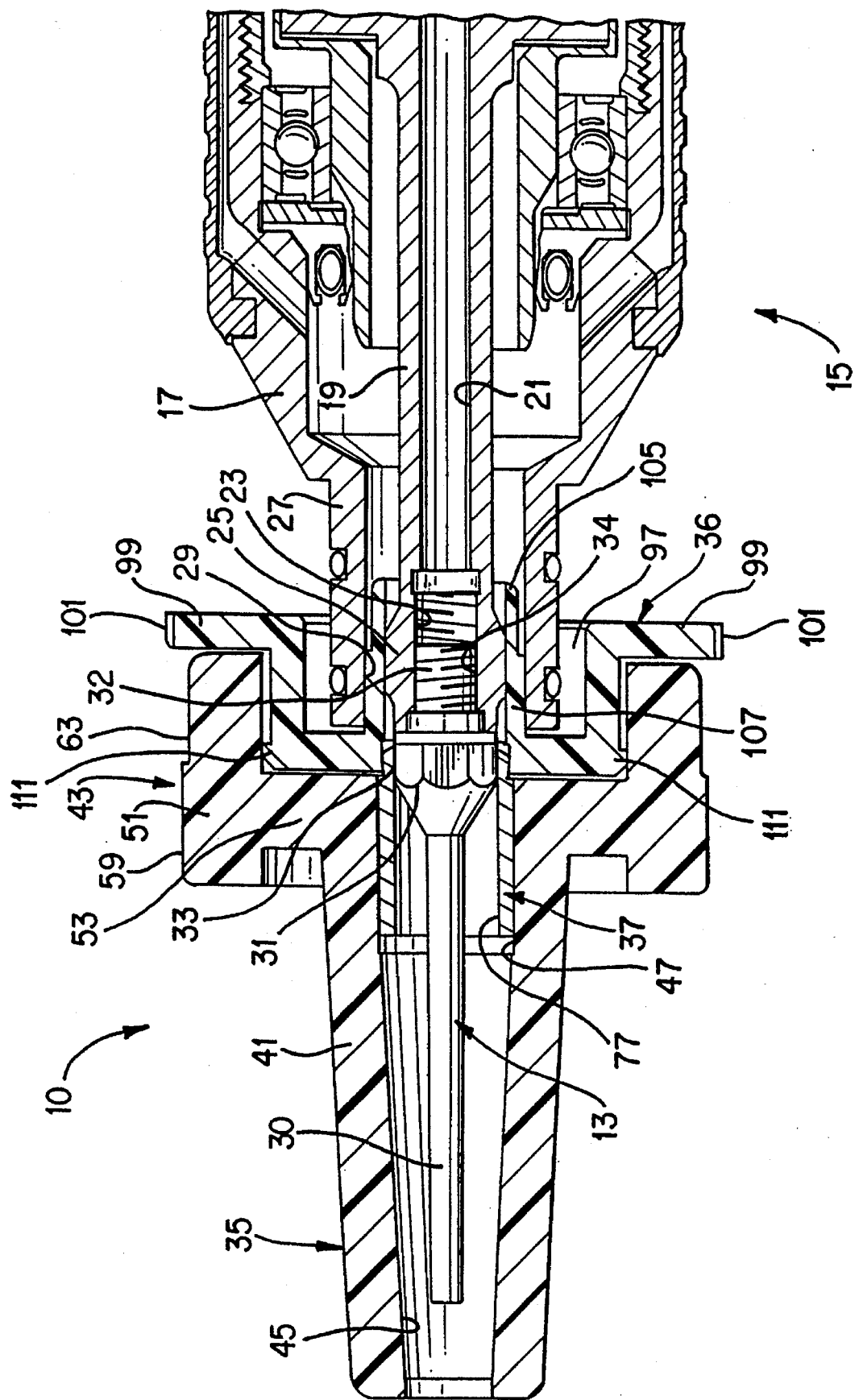
FIG. 13 is a longitudinal cross-sectional view of the wrench installing a tip onto a tool.

The present invention pertains to a wrench 10 (FIGS. 1–3) adapted to install or remove a tip 13 onto or from a tool 15 (FIG. 13). The wrench is specifically adapted to cooperate with certain surgical tools for extracting the natural lens from a patient's eye. Nevertheless, a wrench in accordance with the present invention could be used with other tools which have a similar construction.

Tool 15 comprises a housing 17 and a central rotatable drive shaft 19 (FIG. 13). Shaft 19 includes an internal bore 21 for providing aspiration and/or irrigation conduits (not shown). The distal end of bore 21 is provided with internal threads 23 adapted to mount tip 13. The exterior of shaft 19 is provided with a hex segment 25 adjacent the free end of the shaft. Housing 17 includes a tubular end segment 27 which surrounds shaft 19. A hex socket 29 is formed in the end of segment 27. In the preferred construction, socket 29 is opposed to hex segment 25 of shaft 19. Also, if desired, socket 29 could be offset from hex segment 25, so long as they both remain near the distal end of the tool. In any event, the inner wall of housing 17 is spaced sufficiently from hex segment 25 so that shaft 19 can rotate freely without contacting the housing.

Tip 13 is adapted to be removably attached to the distal end of shaft 19 (FIG. 13). Tip 13 includes a working end 30, a medial base 31, and a mounting shank 32. Working end 30 can have a variety of different designs to effect cutting of the lens or polishing of the capsular bag. Working end 30 preferably includes an internal bore (not shown) for accommodating aspiration and/or irrigation conduits (not shown). Base 31 is an enlarged section which defines a pair of opposite flats 33. Shank 32 is formed with threads 34 which are adapted to matingly engage with threads 23 in shaft 19. In this way, tip 13 can be screwed into shaft 19 for a secure attachment to tool 15.

Wrench 10 comprises a rotary part 35, a locking hub 36, and an insert 37 (FIGS. 1–10). In general, insert 37 is fixedly attached within rotary part 35 to form an integral unit. Rotary part 35 and hub 36 are interconnected to permit rotational and axial movement of rotary part 35 relative to hub 36.

Rotary part 35 (FIGS. 1–5 and 13) is preferably a molded plastic member, although other materials and manufacturing processes could be utilized. Rotary part 35 comprises a spindle 41 and a wheel or coupling structure 43 attached to the front end of spindle 41. Spindle 41 is a tubular member which defines an internal passage 45 having a size sufficient to receive a tip 13 therein. The inner and outer walls of spindle 41 are tapered to accommodate the molding construction. Spindle 41 is preferably elongated to protect the tip from damage, protect the user's hand from injury, and form a handle element to ease manual grasping and manipulation of the wrench. The forward end of passage 45 defines a hex socket 47 for fixedly receiving insert 37 therein (FIGS. 3 and 5).

Figure 1:
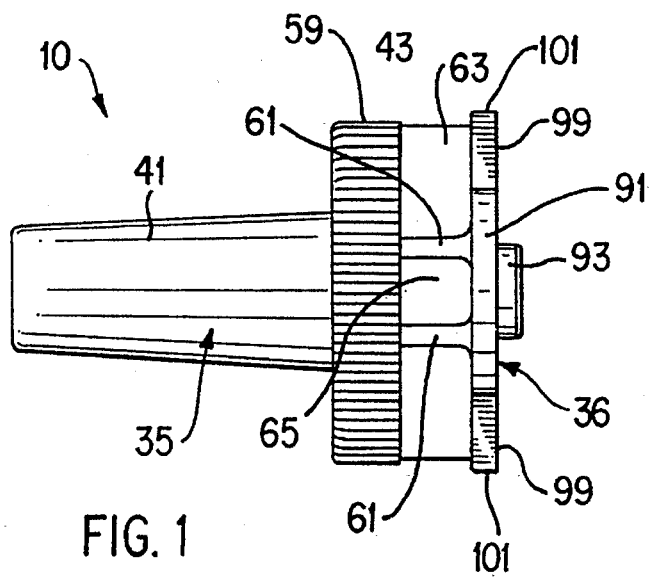
FIG. 1 is a side view of a wrench in accordance with the present invention.
Figure 2:
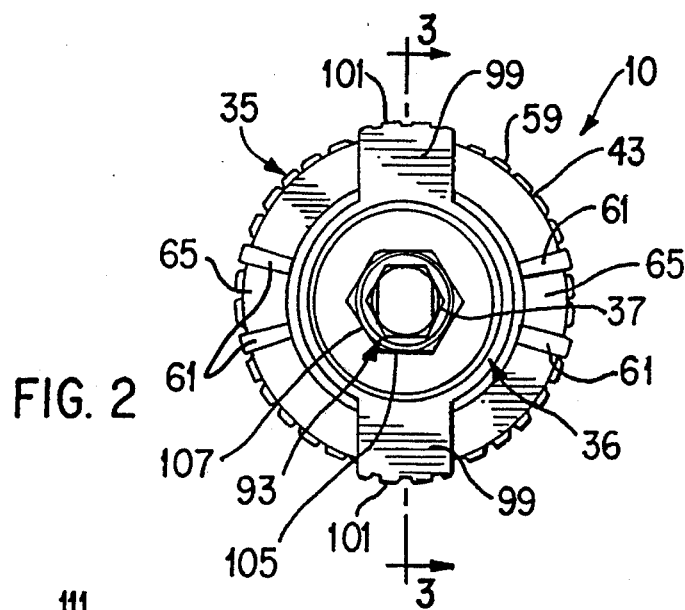
FIG. 2 is a front view of the wrench.
Figure 3:
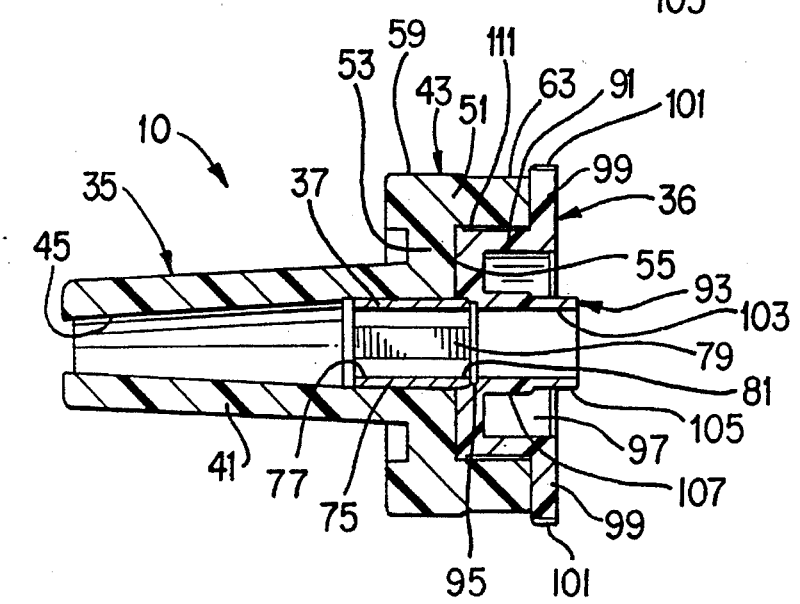
FIG. 3 is a cross-sectional view taken along line 3—3 in FIG. 2.
Figure 4:
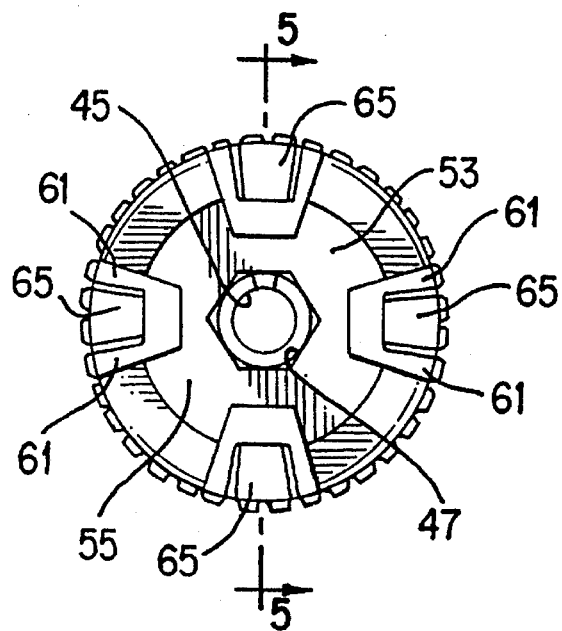
FIG. 4 is a front view of the rotary part of the wrench.
Figure 5:
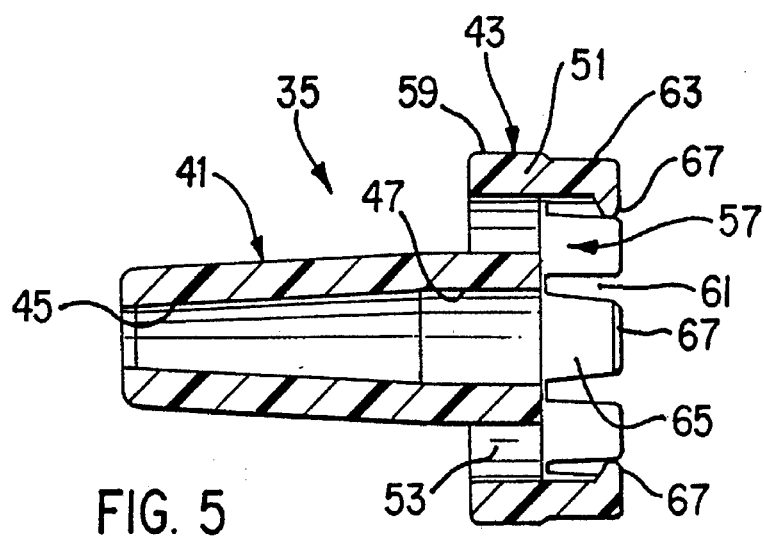
FIG. 5 is a cross-sectional view taken along line 5—5 in FIG. 4.
Figure 6:
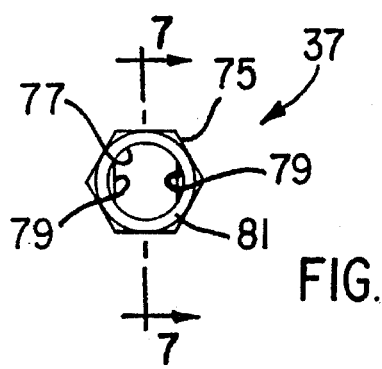
FIG. 6 is a front view of the insert of the wrench.
Figure 7:
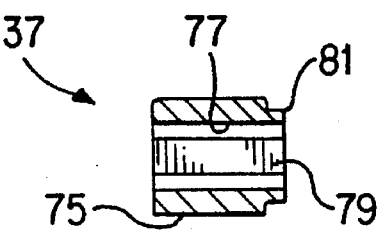
FIG. 7 is a cross-sectional view taken along line 7—7 in FIG. 6.

Wheel 43 includes an annular rim 51 and radial arms 53 (FIGS. 1–5). Rim 51 is attached to the front end of spindle 41 by arms 53 (FIGS. 3 and 4). In the preferred construction, four equally spaced arms 53 are provided. Of course, any number of arms or other similar construction could be used. Arms 53 in cooperation with the front end of spindle 41 form a wall 55. Rim 51 extends forwardly beyond wall 53 to define an open cavity 57 for receiving hub 36 (FIGS. 3 and 5).

The rear portion 59 of rim 51 is ridged to define a portion which can be manually grasped and turned (FIGS. 1 and 2). Of course, other roughening constructions could also be used. A plurality of axial slots 61 are formed in the front portion 63 of rim 51 (FIGS. 2, 4 and 5). Slots 61 preferably taper as they extend rearwardly. Slots 61 are arranged into pairs, such that each pair of slots defines a finger 65 therebetween. Each finger 65 defines an inwardly directed flange 67 to retain hub 36 in cavity 57. Fingers 65 flex outwardly by virtue of slots 61 to facilitate the insertion of hub 36 into cavity 57 during the assembly of wrench 10.

Insert 37 is preferably a unitary metal member, although other materials could be used. Insert 37 has a generally tubular construction which comprises an annular body 75 and a central opening 77 (FIGS. 3, 6–7 and 13). The exterior of body 75 has a hex configuration adapted for mating receipt within hex socket 47. Insert 37 is preferably fixed into socket 47 via a friction fit. Nevertheless other fixing arrangements could be used. Central opening 77 is cylindrical in shape except for a pair of opposing flats 79. Flats 79 are spaced apart to matingly receive complementary flats 33 formed on tip 13. Alternatively, insert 37 may be omitted and hex socket 47 replaced with a socket (not shown) having the same shape as opening 77 of insert 37. A collar 81 which has a reduced diameter, circular configuration is formed on the front end of the insert to provide ample clearance for hub 36 in its fully retracted position.

Hub 36, like rotary part 35, is preferably a molded plastic member. Nevertheless, other materials and fabrication processes could be used. Hub 36 includes an annular outer wall 91 and a central projection 93 positioned concentrically within wall 91 (FIGS. 2–3 and 8–13). A rear wall 95 interconnects outer wall 91 and projection 93 along their rearward ends such that an annular gap 97 is defined between outer wall 91 and projection 93 (FIGS. 11 and 12). A pair of radially extending arms 99 project in opposite directions from the front end of outer wall 91 (FIGS. 9–11). The free ends 101 of arms 99 are preferably ridged to enhance manual grasping and manipulation of the hub. Of course, other roughening constructions could be used.

Projection 93 defines a central opening 103 through which tip 13 can be passed and shaft 19 received (FIGS. 9–13). Opening 103 has a hexagonal cross-section which is sized to matingly receive therein hex segment 25 of shaft 19. The exterior of projection 93 is subdivided into a forward cylindrical section 105 and a rearward hex section 107. Hex section 107 is sized to be matingly received in hex socket 29 of housing 17. In use, projection 93 is received between housing 17 and shaft 19 such that hex opening 103 matingly engages hex segment 25 and hex socket 29 matingly engages hex section 107 (FIG. 13). This construction effectively locks shaft 19 relative to housing 17 to prevent rotation of the shaft when tip 13 is being screwed into the threaded end of bore 21.

The outer diameter of cylindrical portion 105 is no greater than the distance between two opposing flats 109 of hex section 107 (FIG. 9). In this way, the exterior of projection 93 can still be rotated within housing 17 when the user has aligned and engaged hex opening 103 with hex segment 25. Once this first connection with shaft 19 is achieved, the projection can be advanced forward, and rotated if necessary, to align hex section 107 with hex socket 29 (FIG. 13). Arms 99 are provided to facilitate advancement of projection 93 into housing 17. With the projection inserted, the free end of housing 17 is received within gap 97.

The rear end of outer wall 91 is provided with a pair of outwardly extending retaining flanges 111 which wrap around most of the hub (FIGS. 3 and 8–13). Retaining flanges cooperate with finger flanges 67 to retain hub 36 within cavity 57 (FIG. 13). The rear surfaces 113 of retaining flanges 111 are sloped to permit easier entry of hub 36 into cavity 57 during the assembly of the wrench. As can be appreciated, with this construction rotary part 35 can be freely rotated and translated a limited distance relative to hub 36 so that tip 13 can be screwed into shaft 19.

In operation, housing 17 is held in one hand of the user or in an other support. Tip 13 is manually screwed partially into shaft 19 to start the threaded engagement. While shaft 19 can freely rotate within housing 17 when the tool is inactivated, such rotation does not typically inhibit the initial screwing of tip 13. Once the tip is partially installed, wrench 10 is passed over tip 13. While holding arms 99 of hub 36, projection 93 is inserted between housing 17 and shaft 19 to lock the shaft in place (FIG. 13). Rotary part 35 is then adjusted to fit upon flats 33 of tip 13. By grasping ridged portion 59 of rim 51, the user can easily rotate rotary part 35 which, in turns rotates tip 13. This action is continued until tip 13 is tightly screwed into shaft 19. Removal of a tip 13 can be accomplished by practicing the above-described process in the reverse order.

The above discussion concerns the preferred embodiments of the present invention. Various changes can be made without departing from the spirit of the invention. For instance, the various hex sockets and hex segments (or other mating flats) could be formed as virtually any non-circular configuration or other construction which prevented relative rotation. Also, as an example, alterations relating to the structures for easing manipulation or grasping of the device could be made. Further, a wrench in accordance with the present invention could also be used to install or remove a tip onto or from a tool with a fixed shaft. In such a case, the hub projection would simply be received over the shaft without of course locking the shaft relative to the housing.

We claim:

1. A wrench for attaching a tip having a threaded shank and a non-circular portion to a tool including a housing having a non-circular interior end and a rotatable shaft within the housing having a non-circular exterior segment and a threaded bore, said wrench comprising:

a hub including a projection and an opening extending through said projection, at least a portion of said opening being defined by a non-circular inner wall adapted to matingly receive the non-circular exterior segment of the shaft, and at least a portion of said projection having an outer non-circular section adapted to be matingly received within the non-circular interior end of the housing so that said projection engages the shaft and the housing to thereby prevent rotation of the shaft relative to the housing; and a rotary part being rotatable independently of said hub and including a passage for receiving the tip, said passage being generally aligned with said opening of said hub, at least a portion of said passage being defined by a non-circular interior wall positioned rearward of said non-circular inner wall and said outer non-circular section of said hub, said non-circular interior wall of said passage being adapted to matingly receive the non-circular portion of the tip so that rotation of said rotary part causes the threaded shank of the tip to be screwed into the threaded bore of the shank.

2. A wrench in accordance with claim 1 wherein said projection of said hub further includes a free end which has an outer circular section adjacent said outer non-circular section whereby said outer circular section functions as a guide in the housing prior to receipt of said outer non-circular section therein.

3. A wrench in accordance with claim 1 further comprising means for interconnecting said rotary part and said hub to provide free rotation and limited translation of said rotary part relative to said hub.

4. A wrench in accordance with claim 1 in which said rotary part includes a handle element with a front end and a coupling structure fixed to said front end of said handle element to define a cavity for receiving said hub.

5. A wrench in accordance with claim 4 in which said outer wall includes a roughened exterior portion for effecting manual rotation of said rotary part.

6. A wrench for attaching a tip having a threaded shank and a non-circular portion to a tool including a housing having a non-circular interior end and a rotatable shaft within the housing having a non-circular exterior segment and a threaded bore, said wrench comprising:

a hub including a projection, a wall surrounding said projection and an opening extending through said projection, at least a portion of said opening being defined by a non-circular inner wall adapted to matingly receive the non-circular exterior segment of the shaft, and at least a portion of said projection having an outer non-circular section adapted to be matingly received within the non-circular interior end of the housing so that said projection engages the shaft and the housing to thereby prevent rotation of the shaft relative to the housing; and a rotary part including a passage for receiving the tip, said passage being generally aligned with said opening of said hub, at least a portion of said passage being defined by a non-circular interior wall adapted to matingly receive the non-circular portion of the tip so that rotation of said rotary part causes the threaded shank of the tip to be screwed into the threaded bore of the shank, said rotary part further including a handle element with a front end and a coupling structure fixed to said front end of said handle element to define a cavity for receiving said wall of said hub.

7. A wrench in accordance with claim 6 in which said rotary part includes at least one first flange extending radially inward from a front end of said coupling structure, and at least one second flange extending radially outward from a rear end of said wall of said hub, said first and second flanges forming complementary stops for preventing separation of said rotary part and said hub.

8. A wrench in accordance with claim 1 in which said rotary part includes an insert member which defines said non-circular interior wall.

9. A wrench comprising:

a rotary part including a handle element and a coupling structure fixedly attached to one end of said handle element, said handle element including an axial passage open on at least said one end, said passage having at least a non-circular portion adjacent said one end, said coupling structure including a forwardly opening cavity concentric with said axial passage; and a hub received within said cavity and including a projection and an axial opening extending through said projection, said axial opening being in alignment with said axial passage of said rotary part, at least a portion of said axial opening being defined by a non-circular inner wall, and at least a portion of said projection having an outer non-circular section; and said rotary part and said hub including connecting structures which interconnect said rotary part and said hub such that said rotary part is freely rotatable about said hub and translatable a limited distance relative to said hub.

10. A wrench in accordance with claim 9 wherein said projection of said hub further includes a free end which has an outer circular section adjacent said outer non-circular section.

11. A wrench in accordance with claim 9 wherein said coupling structures include at least one first flange extending radially inward from a front end of said coupling structure, and at least one second flange extending radially outward from a rear end of said hub, said first and second flanges forming complementary stops for preventing separation of said rotary part and said hub.

12. A wrench in accordance with claim 9 in which said coupling structure includes a roughened exterior portion for effecting manual rotation of said rotary part.

13. An assembling system comprising:

a tip having a threaded shank and a non-circular portion;

a tool including a housing having a non-circular interior end and a rotatable shaft within the housing having a non-circular exterior segment and a threaded bore; and a wrench for attaching said tip to said end of said shaft, said wrench comprising:

a hub including a projection and an opening extending through said projection, at least a portion of said opening being defined by a non-circular inner wall adapted to matingly receive the non-circular exterior segment of the shaft, and at least a portion of said projection having an outer non-circular section adapted to be matingly received within the non-circular interior end of the housing so that said projection engages the shaft and the housing to thereby prevent rotation of the shaft relative to the housing; and a rotary part including a passage for receiving the tip, said passage being generally aligned with said opening of said hub, at least a portion of said passage being defined by a non-circular interior wall adapted to matingly receive the non-circular portion of the tip so that rotation of said rotary part causes the threaded shank of the tip to be screwed into the threaded bore of the shank.

14. An assembly system in accordance with claim 13 wherein said projection of said hub further includes a free end which has an outer circular section adjacent said outer non-circular section whereby said outer circular section functions as a guide in the housing prior to receipt of said outer non-circular section therein.

* * * * *